United States Patent

Borzatta et al.

Patent Number: 5,466,803
Date of Patent: Nov. 14, 1995

[54] PIPERIDINE-TRIAZINE COMPOUNDS SUITABLE FOR USE AS STABILIZERS FOR ORGANIC MATERIALS

[75] Inventors: Valerio Borzatta, Bologna; Graziano Vignali, Sasso Marconi - Bologna, both of Italy

[73] Assignee: Ciba-Geigy Corporation, Tarrytown, N.Y.

[21] Appl. No.: 191,575

[22] Filed: Feb. 3, 1994

[30] Foreign Application Priority Data

Feb. 11, 1993 [IT] Italy ................... MI93A0247

[51] Int. Cl.[6] .............. C07D 251/42; C07D 251/48; C07D 251/54; C07D 251/66
[52] U.S. Cl. .............. 544/198; 540/454; 540/460; 540/488; 540/492; 544/194; 544/195
[58] Field of Search ............ 544/194, 195, 544/198; 540/454, 460, 488, 492

[56] References Cited

U.S. PATENT DOCUMENTS

| | | | |
|---|---|---|---|
| 4,086,204 | 4/1978 | Cassandrini et al. | 544/196 |
| 4,315,859 | 2/1982 | Nikles | 544/198 |
| 4,331,586 | 5/1982 | Hardy | 525/186 |
| 4,335,242 | 6/1982 | Wiezer et al. | 544/198 |
| 4,412,020 | 10/1983 | Loffelman et al. | 524/100 |
| 4,459,395 | 7/1984 | Cantatore | 544/212 |
| 4,477,615 | 10/1984 | Raspanti et al. | 544/198 |
| 4,547,548 | 10/1985 | Cantatore | 525/186 |
| 4,696,961 | 9/1987 | Cantatore | 524/100 |
| 4,889,882 | 2/1989 | Nelson et al. | 524/100 |
| 5,187,275 | 2/1993 | Borzatta et al. | 544/207 |
| 5,310,767 | 5/1994 | Borzatta et al. | 544/357 |

FOREIGN PATENT DOCUMENTS

| | | |
|---|---|---|
| 0117229 | 8/1984 | European Pat. Off. . |
| 0217149 | 4/1987 | European Pat. Off. . |
| 0354185 | 2/1990 | European Pat. Off. . |
| 0435828 | 7/1991 | European Pat. Off. . |
| 0462069 | 12/1991 | European Pat. Off. . |
| 0468928 | 1/1992 | European Pat. Off. . |
| 0479724 | 4/1992 | European Pat. Off. . |
| 0548015 | 6/1993 | European Pat. Off. . |
| 63-196654 | 8/1988 | Japan . |

Primary Examiner—Yogendra N. Gupta
Attorney, Agent, or Firm—Luther A. R. Hall; Michele A. Kovaleski

[57] ABSTRACT

Novel piperidine-triazine compounds of the formula (I) useful as light stabilizers, heat stabilizers and antioxidants for organic materials.

The meanings of $R_1$, $R_2$, $R_3$, $R_4$, $X_1$, $X_2$, $X_3$, $Y_1$, $Y_2$, M and N are defined in the text.

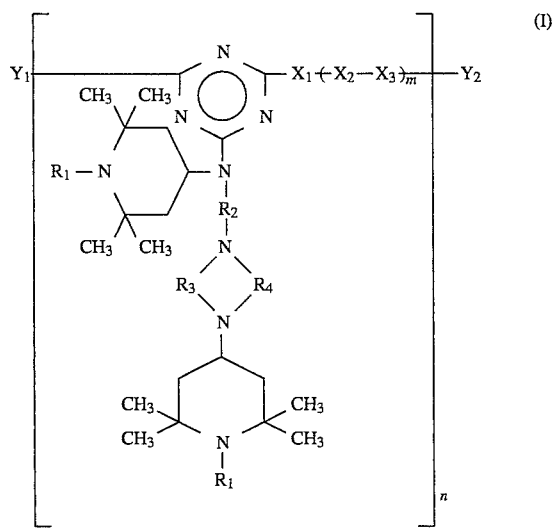

6 Claims, No Drawings

PIPERIDINE-TRIAZINE COMPOUNDS SUITABLE FOR USE AS STABILIZERS FOR ORGANIC MATERIALS

The present invention relates to novel piperidine-triazine compounds, their use as light stabilisers, heat stabilisers and antioxidants for organic materials, especially synthetic polymers, and organic materials thus stabilised.

It is known to use, as stabilisers for synthetic polymers, triazine oligomers and co-oligomers containing 2,2,6,6-tetramethylpiperidine groups, as claimed in U.S. Pat. Nos. 4,086,204, 4,315,859, 4,331,586, 4,335,242, 4,412,020, 4,459,395, 4,477,615, 4,547,548, 4,696,961 and 4,889,882, European Patents 117 229, 217 149, 354 185, 435 828, 462 069, 468 928, 479 724 and 548 015 and Japanese Patent 63-196 654.

The present invention relates to novel compounds of the formula (I)

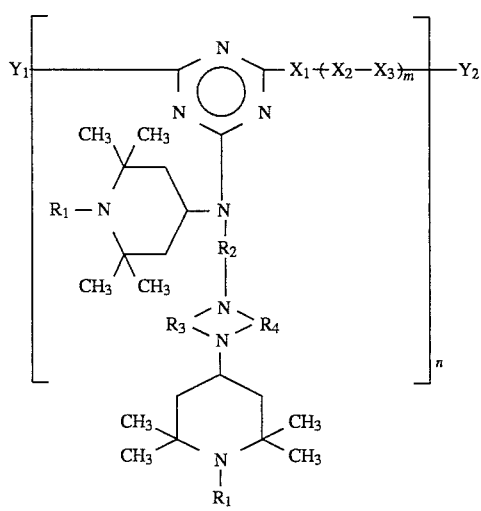

in which $R_1$ is hydrogen, $C_1$–$C_8$alkyl, O., OH, $CH_2CN$, $C_1$–$C_{18}$alkoxy, $C_5$–$C_{12}$cycloalkoxy, $C_3$–$C_6$alkenyl, or $C_7$–$C_9$phenylalkyl, which is unsubstituted or substituted on the phenyl by 1, 2 or 3 $C_1$–$C_4$alkyls, or $C_1$–$C_8$acyl;

$R_2$ and $R_3$, which may be identical or different, are $C_2$–$C_3$alkylene;

$R_4$ is —CO—, —COCO—, —COCH$_2$CO— or —CH$_2$CO—;

$X_1$ and $X_3$, which may be identical or different, are one of the groups of the formula (IIa)–(IIe)

—$A_1$—$R_5$—$A_2$—, (IIa)

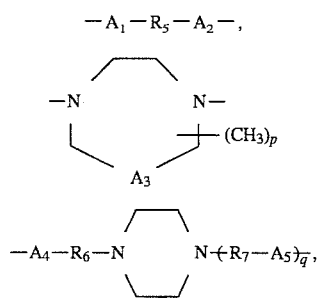

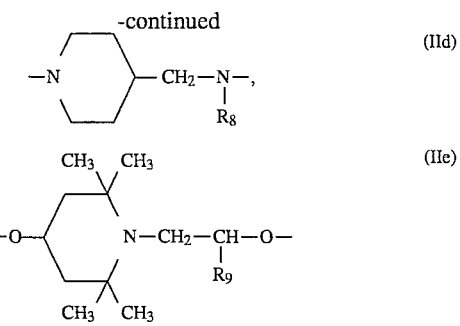

in which $A_1$, $A_2$, $A_4$ and $A_5$, which may be identical or different, are —O— or

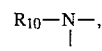

where $R_{10}$ is hydrogen, $C_1$–$C_{18}$alkyl, $C_5$–$C_{12}$cycloalkyl which is unsubstituted or substituted by 1, 2 or 3 $C_1$–$C_4$alkyls, $C_7$–$C_9$phenylalkyl which is unsubstituted or substituted on the phenyl by 1, 2 or 3 $C_1$–$C_4$alkyls, or a group of the formula (III)

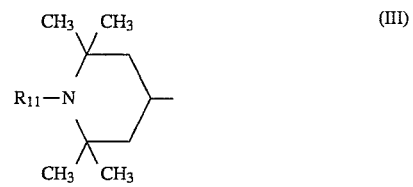

where $R_{11}$ has any one of the meanings given for $R_1$;

$R_5$ is $C_2$–$C_{12}$alkylene, $C_4$–$C_{12}$alkylene interrupted by 1, 2 or 3 oxygen atoms or by 1 or 2

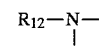

groups, where $R_{12}$ has any one of the meanings given for $R_{10}$ or is $C_1$–$C_8$acyl or ($C_1$–$C_8$alkoxy)carbonyl, or $R_5$ is $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), $C_2$–$C_4$alkylidenedi($C_5$–$C_7$cycloalkylene), phenylene, phenylenedi($C_1$–$C_4$alkylene), $C_1$–$C_4$alkylenediphenylene or $C_2$–$C_4$alkylidenediphenylene, each phenylene group being unsubstituted or substituted by 1 or 2 $C_1$–$C_4$alkyls, or $R_5$ is a group of the formula (IV)

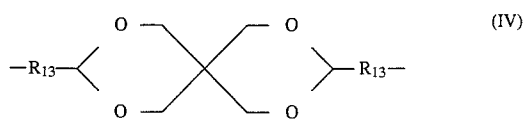

where $R_{13}$ is $C_2$–$C_6$alkylene;

$A_3$ is a direct bond or —CH$_2$—, p is zero, 1, 2 or 3;

$R_6$ and $R_7$, which may be identical or different, are $C_2$–$C_6$alkylene, q is zero or 1;

$R_8$ is as defined above for $R_{10}$ and $R_9$ is hydrogen or $C_1$–$C_4$alkyl;

$X_2$ is $C_2$-$C_{12}$alkylene, $C_4$-$C_{12}$alkylene interrupted by 1, 2 or 3 oxygen atoms, 2-hydroxytrimethylene, phenylenedimethylene, carbonyl or one of the groups of the formula (Va)–(Ve)

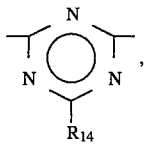  (Va)

$-CO-R_{15}-CO-$,  (Vb)
$-COO-R_{16}-OOC-$,  (Vc)
$-(CH_2)_r-CO-$,  (Vd)
$-CONH-R_{17}-NHCO-$  (Ve)

in which $R_{14}$ is one of the groups of the formula (VIa)–(VId)

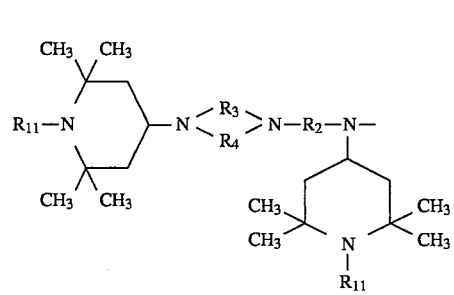  (VIa)

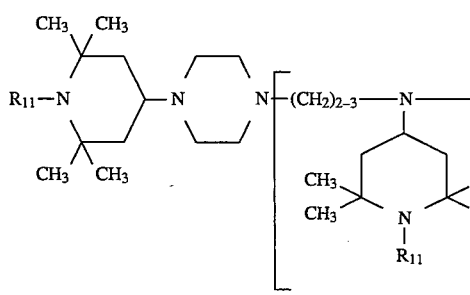  (VIb)

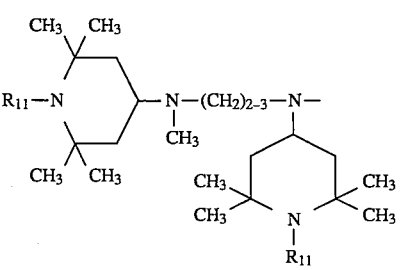  (VIc)

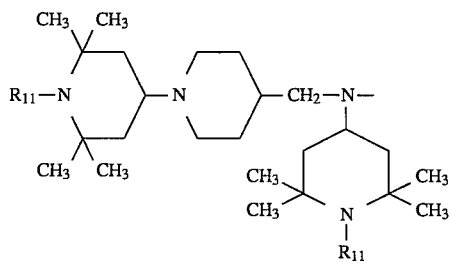  (VId)

where $R_2$, $R_3$, $R_4$ and $R_{11}$ are as defined above and s is zero or 1, or $R_{14}$ is a group of formula (VII)

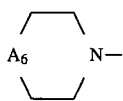  (VII)

where $A_6$ is a direct bond, $-O-$, $-CH_2-$, $-CH_2CH_2-$ or

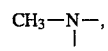

or $R_{14}$ is an $R_{18}O-$ or

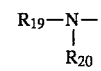

group, where $R_{18}$, $R_{19}$ and $R_{20}$, which may be identical or different, have any one of the meanings given for $R_{10}$ or are $C_3$-$C_{18}$alkenyl, tetrahydrofurfuryl, phenyl which is unsubstituted or substituted by 1, 2 or 3 $C_1$-$C_4$alkyls, or by $C_1$-$C_4$alkoxy, or $C_2$-$C_4$alkyl which is substituted in the 2, 3 or 4-position by $C_1$-$C_8$alkoxy or by di($C_1$-$C_4$alkyl)amino or by a group of formula (VII);

$R_{15}$ is a direct bond, $C_1$-$C_{12}$alkylene, $C_2$-$C_{20}$alkylidene, cyclohexylene, methylcyclohexylene or phenylene; $R_{16}$ has any one of the meanings given for $R_5$, r is an integer from 1 to 10 and $R_{17}$ has any one of the meanings given for $R_5$ or is

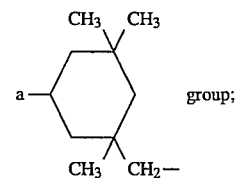

group;

m is zero, 1, 2, 3 or 4 and n is a number from 1 to 50 with the restriction that n is 1 only if m is other than zero;

$Y_1$ and $Y_2$ are end groups which can have various meanings depending on the type and the molar ratios of the reagents employed in the preparation. In particular, $Y_1$ can be Cl, OH, ONa, OK, an $R_{14}$ group or a $-X_1Z$ or $-X_3Z$ group, where Z is hydrogen, methyl, benzyl, $C_1$-$C_8$acyl or ($C_1$-$C_8$alkoxy)carbonyl and $Y_2$ can be Z, a

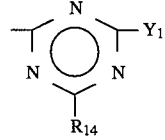

group or a $-X_2OH$ group.

Examples of alkyl containing not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of $C_2$–$C_4$alkyl substituted by $C_1$–$C_8$alkoxy, preferably by $C_1$–$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$–$C_4$alkyl substituted by di($C_1$–$C_4$alkyl)amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Preferred examples of $C_2$–$C_4$alkyl substituted by a group of formula (VII) are the

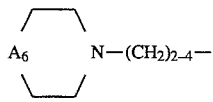

groups; the

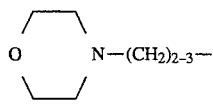

group is particularly preferred.

Examples of alkoxy containing not more than 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. Preferred examples of $R_1$ and $R_{11}$ are $C_6$–$C_{12}$alkoxy, in particlar heptoxy and octoxy.

Examples of $C_5$–$C_{12}$cycloalkyl which is unsubstituted or substituted by 1,2 or 3 $C_1$–$C_4$alkyls are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl.

Cyclohexyl which is unsubstituted or substituted is preferred.

For $R_1$ and $R_{11}$, examples of $C_5$–$C_{12}$cycloalkoxy are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl containing not more than 18 carbon atoms are allyl, 2-methylallyl, butenyl, hexenyl, decenyl, undecenyl and octadecenyl.

The alkenyls in which the carbon atom in position 1 is saturated, are preferred; allyl is particularly preferred.

Examples of substituted phenyl are methylphenyl, dimethylphenyl, trimethylphenyl, t-butylphenyl, di-t-butylphenyl, 3,5-di-t-butyl-4-methylphenyl, methoxyphenyl and ethoxyphenyl.

Examples of $C_7$–$C_9$phenylalkyl which is unsubstituted or substituted on the phenyl by 1, 2 or 3 $C_1$–$C_4$alkyls are benzyl, methylbenzyl, dimethylbenzyl, trimethylbenzyl, t-butylbenzyl and 2-phenylethyl. Benzyl is preferred.

$R_1$, $R_{11}$, $R_{12}$ and Z, as acyl containing not more than 8 carbon atoms, can be an aliphatic or aromatic group. Representative examples are formyl, acetyl, propionyl, butyryl, pentanoyl, hexanoyl, heptanoyl, octanoyl, benzoyl, acryloyl and crotonyl. Preferred are $C_1$–$C_8$-alkanoyl, $C_3$–$C_8$-alkenoyl and benzoyl, particularly acetyl.

Examples of alkylene containing not more than 12 carbon atoms are methylene, ethylene, propylene, trimethylene, tetramethylene, pentamethylene, 2,2-dimethyltrimethylene, hexamethylene, trimethylhexamethylene, octamethylene, decamethylene and dodecamethylene.

Preferred examples of $C_2$–$C_{20}$alkylidene are ethylidene, propylidene, butylidene, pentylidene, heptylidene, nonylidene, undecylidene, tridecylidene, pentadecylidene, heptadecylidene and nonadecylidene.

Examples of $C_4$–$C_{12}$alkylene interrupted by 1, 2 or 3 oxygen atoms are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl, 3,6,9-trioxaundecane-1,11-diyl and 4,7,10-trioxatridecane-1,13-diyl.

If $R_5$, $R_{16}$ and $R_{17}$ are $C_4$–$C_{12}$alkylene interrupted by 1 or 2

groups, representative examples are the groups

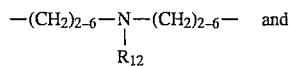

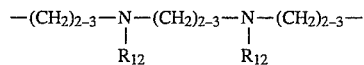

Representative examples of groups containing 1 or 2 $C_5$–$C_7$cycloalkylene groups are cyclohexylene, methylcyclohexylene, cyclohexylenedimethylene, methylenedicyclohexylene and isopropylidenedicyclohexylene.

Representative examples of groups containing 1 or 2 phenylene groups which are unsubstituted or substituted are phenylene, methylphenylene, dimethylphenylene, phenylenedimethylene, methylenediphenylene, isopropylidenediphenylene.

The preferred meanings of $R_1$ and $R_{11}$ are hydrogen, $C_1$–$C_4$alkyl, OH, $C_6$–$C_{12}$alkoxy, $C_5$–$C_8$cycloalkoxy, allyl, benzyl or acetyl, in particular hydrogen or methyl.

Preferred compounds of the formula (I) are those in which $R_2$ and $R_3$, which may be identical or different, are $C_2$–$C_3$alkylene, $R_4$ is —CO—, —COCO— or —COCH$_2$CO—;

$X_1$ and $X_3$, which may be identical or different, are one of the groups of formula (IIa)–(IIe), in which $A_1$, $A_2$, $A_4$ and $A_5$, which may be identical or different, are —O— or

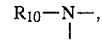

where $R_{10}$ is hydrogen, $C_1$–$C_{12}$alkyl, $C_5$–$C_8$cycloalkyl which is unsubstituted or substituted by 1, 2 or 3 $C_1$–$C_4$alkyls, benzyl which is unsubstituted or substituted on the phenyl by 1, 2 or 3 $C_1$–$C_4$alkyls, or a group of formula (III), $R_5$ is $C_2$–$C_{10}$alkylene, $C_4$–$C_{10}$alkylene interrupted by 1, 2 or 3 oxygen atoms or by 1 or 2

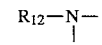

groups, where $R_{12}$ has any one of the meanings given for $R_{10}$ or is $C_1$–$C_4$acyl or ($C_1$–$C_4$alkoxy)carbonyl, or $R_5$ is cyclohexylene, cyclohexylenedimethylene, methylenedicyclohexylene, isopropylidenedicyclohexylene, phenylene, methylphenylene, phenylenedimethylene, methylenediphenylene or isopropylidenediphenylene, or $R_5$ is a group of formula (IV), where $R_{13}$ is $C_2$–$C_4$alkylene;

$A_3$ is a direct bond or —$CH_2$—, p is zero, 1, 2 or 3, $R_6$ and $R_7$, which may be identical or different, are $C_2$–$C_4$alkylene, q is zero or 1, $R_8$ is as defined above for $R_{10}$ and $R_9$ is hydrogen or $C_1$–$C_4$alkyl;

$X_2$ is $C_2$–$C_{10}$alkylene, $C_4$–$C_{10}$alkylene interrupted by 1, 2 or 3 oxygen atoms, 2-hydroxytrimethylene, phenylenedimethylene or one of the groups of formula (Va)–(Ve), in which $R_{14}$ is one of the groups of formula (VIa)–(VId), where $R_2$, $R_3$ and $R_4$ are as defined above and s is zero or 1, or $R_{14}$ is 1-pyrrolidyl, 1-piperidyl, 4-morpholinyl or 1-hexahydroazepinyl or an $R_{18}$O— or

group, where $R_{18}$, $R_{19}$ and $R_{20}$, which may be identical or different, have any one of the meanings given for $R_{10}$ or are $C_3$–$C_{12}$alkenyl, tetrahydrofurfuryl, phenyl which is unsubstituted or substituted by 1, 2 or 3 $C_1$–$C_4$alkyls, or $C_2$–$C_3$alkyl substituted in the 2 or 3 position by $C_1$–$C_4$alkoxy or by di($C_1$–$C_4$alkylamino) or by a 1-pyrrolidyl, 1-piperidyl, 4-morpholinyl or 1-hexahydroazepinyl group;

$R_{15}$ is a direct bond, $C_1$–$C_{10}$alkylene, $C_2$–$C_{14}$alkylidene, cyclohexylene or phenylene;

$R_{16}$ has any one of the meanings given for $R_5$, r is an integer from 1 to 5 and $R_{17}$ has any one of the meanings given for $R_5$ or is a

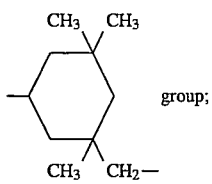

group;

m is zero, 1, 2 or 3 and n is a number from 1 to 30, with the restriction that n is 1 only if m is other than zero;

$Y_1$ is Cl, OH, ONa, OK, an $R_{14}$ group or a —$X_1$Z or —$X_3$Z group, where Z is hydrogen, methyl, benzyl, $C_1$–$C_4$acyl or ($C_1$–$C_4$alkoxy)carbonyl and $Y_2$ is Z, a

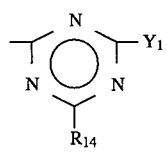

group or an —$X_2$OH group.

Particularly preferred compounds of formula (I) are those in which $R_2$ and $R_3$, which may be identical or different, are $C_2$–$C_3$alkylene and $R_4$ is —CO— or —COCO—;

$X_1$ and $X_3$, which may be identical or different, are one of the groups of formula (IIa)–(IIe) in which $A_1$, $A_2$, $A_4$ and $A_5$, which may be identical or different, are —O— or

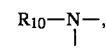

where $R_{10}$ is hydrogen, $C_1$–$C_8$alkyl, cyclohexyl which is unsubstituted or substituted by 1, 2 or 3 $C_1$–$C_4$alkyls, benzyl or a group of formula (III); $R_5$ is $C_2$–$C_8$alkylene, $C_4$–$C_{10}$alkylene interrupted by 1, 2 or 3 oxygen atoms or by an

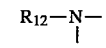

group, where $R_{12}$ is hydrogen, methyl, acetyl or ($C_1$–$C_2$alkoxy)carbonyl, or $R_5$ is cyclohexylene, cyclohexylenedimethylene, methylenedicyclohexylene, phenylenedimethylene or isopropylidenediphenylene, or $R_5$ is a group of formula (IV), where $R_{13}$ is $C_3$–$C_4$alkylene;

$A_3$ is a direct bond or —$CH_2$—, p is zero or 1, $R_6$ and $R_7$, which may be identical or different, are $C_2$–$C_3$alkylene, q is zero or 1, $R_8$ is as defined above for $R_{10}$ and $R_9$ is hydrogen or methyl;

$X_2$ is $C_2$–$C_8$alkylene, $C_4$–$C_8$alkylene interrupted by 1 or 2 oxygen atoms, 2-hydroxytrimethylene, phenylenedimethylene or one of the groups of formula (Va)–(Ve) in which $R_{14}$ is one of the groups of formula (VIa)–(VId), where $R_2$, $R_3$ and $R_4$ are as defined above and s is zero or 1, or $R_{14}$ is a 4-morpholinyl group or an $R_{18}$O— or

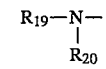

group, where $R_{18}$, $R_{19}$ and $R_{20}$, which may be identical or different, have any one of the meanings given for $R_{10}$ or are allyl, undecenyl, tetrahydrofurfuryl, phenyl or $C_2$–$C_3$alkyl, substituted in the 2 or 3 position by $C_1$–$C_4$alkoxy, by dimethylamino, by diethylamino or by a 4-morpholinyl group;

$R_{15}$ is a direct bond, $C_1$–$C_8$alkylene, $C_2$–$C_6$alkylidene, cyclohexylene or phenylene;

$R_{16}$ is C2-$C_8$alkylene, $C_4$–$C_{10}$alkylene interrupted by 1, 2 or 3 oxygen atoms, cyclohexylenedimethylene, isopropylidenedicyclohexylene or isopropylidenediphenylene, r is an integer from 1 to 4, $R_{17}$ has any one of the meanings given for $R_5$ or is methylphenylene,

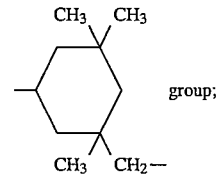

group;

m is zero, 1 or 2 and n is a number from 1 to 20 with the restriction that n is 1 only if m is other than zero;

$Y_1$ is OH, ONa, OK, an $R_{14}$ group or a —$X_1$Z or —$X_3$Z group, where Z is hydrogen, methyl, acetyl or ($C_1$-$C_4$alkoxy)carbonyl and $Y_2$ is Z, a

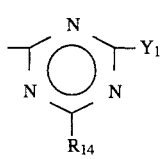

group or an —$X_2OH$ group.

Compounds of formula (I) of special interest are those in which $R_2$ and $R_3$, which may be identical or different, are ethylene or trimethylene and $R_4$ is —CO— or —COCO—;

$X_1$ and $X_3$, which may be identical or different, are one of the groups of formula (IIa)–(IIe) in which $A_1$, $A_2$, $A_4$ and $A_5$, which may be identical or different, are —O— or

where $R_{10}$ is hydrogen, $C_1$-$C_4$alkyl, cyclohexyl, benzyl or a group of formula (III);

$R_5$ is $C_2$-$C_6$alkylene, $C_6$-$C_{10}$alkylene interrupted by 2 or 3 oxygen atoms, cyclohexylenedimethylene, methylenedicyclohexylene or phenylenedimethylene, or $R_5$ is a group of formula (IV), where $R_{13}$ is trimethylene;

$A_3$ is a direct bond, p is zero or 1, $R_6$ and $R_7$, which may be identical or different, are ethylene or trimethylene, q is zero or 1, $R_8$ is as defined above for $R_{10}$ and $R_9$ is hydrogen or methyl;

$X_2$ is $C_2$-$C_6$alkylene, 2-hydroxytrimethylene, phenylenedimethylene or one of the groups of formula (Va)–(Ve) in which $R_{14}$ is a group of formula (VIa), with $R_2$, $R_3$ and $R_4$ as defined above, or a 4-morpholinyl group or an $R_{18}O$— or

group, where $R_{18}$ is $C_1$-$C_4$alkyl, cyclohexyl, allyl, phenyl, benzyl or a group of formula (III) and $R_{19}$ and $R_{20}$, which may be identical or different, are as defined above for $R_{10}$;

$R_{15}$ is a direct bond or $C_1$-$C_6$alkylene, $R_{16}$ is $C_4$-$C_6$alkylene, r is 1 or 2 and $R_{17}$ is $C_2$-$C_6$alkylene or a

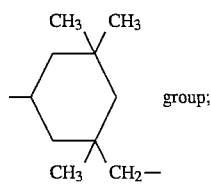

group;

m is zero, 1 or 2 and n is a number from 1 to 15 with the restriction that n is 1 only if m is other than zero;

$Y_1$, is OH, ONa, OK, an $R_{14}$ group or a —$X_1Z$ or —$X_3Z$ group, where Z is hydrogen, methyl, acetyl or ($C_1$-$C_2$alkoxy)carbonyl and $Y_2$ is Z, a

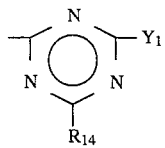

group or a —$X_2OH$ group.

The compounds of formula (I) of particular interest are those in which $R_1$ and $R_{11}$, which may be identical or different, are hydrogen or methyl, $R_2$ and $R_3$ are ethylene, $R_4$ is —CO— or —COCO—;

$X_1$ is one of the groups of formula (IIa)–(IIc) in which $A_1$, $A_2$ and $A_4$ are an

group, where $R_{10}$ is hydrogen, methyl, ethyl or a group of formula (III), or $A_2$ is —O—;

$R_5$ is —$(CH_2)_{2-6}$— or —$(CH_2)_3$—O—$(CH_2)_{2-4}$—O—$(CH_2)_3$—;

$A_3$ is a direct bond, p and q are zero and $R_6$ is ethylene;

n is a number from 2 to 10, $Y_1$ is OH, ONa, OK, an $R_{14}$ group or a —$X_1Z$ group, with Z being hydrogen or methyl, and $Y_2$ is hydrogen, methyl or a

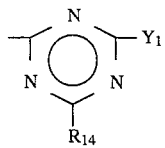

group and $R_{14}$ is a group of formula (VIa) with $R_2$, $R_3$, $R_4$ and $R_{11}$ as defined above.

The compounds of formula (I) can be prepared in accordance with known per se, for example as described in U.S. Pat. Nos. 4,086,204, 4,459,395 and 4,547,548, by reacting, in any sequence and in accordance with the appropriate molar ratios, cyanuric chloride with compounds of formula (VIIIa)–(VIIId)

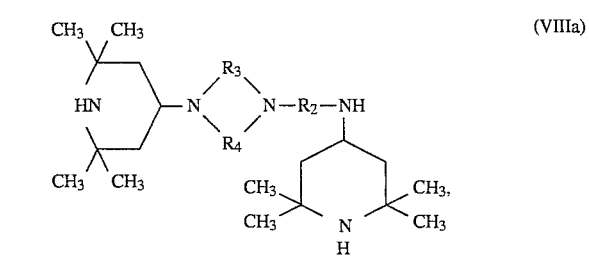

in which $R_2$, $R_3$, $R_4$, $X_1$, $X_2$ and $X_3$ are as defined above and $G_1$ and $G_2$ are Cl, Br or $C_1$-$C_4$alkoxy or $G_1$-$X_2$-$G_2$ represents epichlorohydrin or a diisocyanate OCN—$R_{17}$—NCO, with $R_{17}$ as defined above.

In this way, the compounds of formula (I) with $R_1$=H are obtained, from which the corresponding compounds with $R_1 \neq H$ can subsequently be obtained.

Advantageously, the reactions are carried out in an inert organic solvent, for example toluene, xylene or trimethylbenzene, working at a temperature of −20° to 200° C., preferably from −10° to 180° C.

The compounds of formula (VIIIa) can be prepared as described in European Patent Application 548 015, by reacting a compound of formula (IX) with a compound of formula (X) in which $G_3$ is $NH_2$ or $C_1$–$C_4$alkoxy

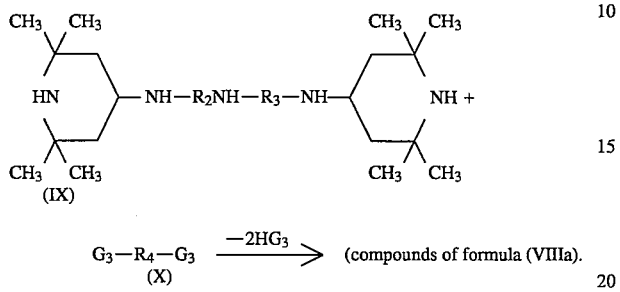

$$G_3-R_4-G_3 \xrightarrow{-2HG_3} \text{(compounds of formula (VIIIa)).}$$
(X)

The compounds of formula (IX) can be obtained in accordance with known processes by reductive alkylation of a triamine $H_2N$—$R_2$—$NH$—$R_3$—$NH_2$ with 2,2,6,6-tetramethyl-4-piperidone in the presence of a hydrogenation catalyst.

The other reagents required for the preparation of the compounds of formula (I) are commercially available or can be prepared in accordance with known processes.

As pointed out initially, the compounds of formula (I) are very effective in improving the light resistance, heat resistance and oxidation resistance of organic materials, in particular synthetic polymers and copolymers.

Examples of such organic materials which can be stabilised are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The compounds of formula (I) are particularly suitable for improving the light stability, heat stability and stability to oxidation of polyolefins, particularly polyethylene and polypropylene.

The compounds of formula (I) can be used in mixtures with organic materials in various proportions depending on the nature of the material to be stabilised, on the end use and on the presence of other additives.

In general, it is appropriate to use, for example 0.01 to 5% by weight of the compounds of formula (I), relative to the weight of the material to be stabilised, preferably between 0.05 and 1%.

In general, the compounds of formula (I) can be incorporated in the polymeric materials before, during or after the polymerisation or crosslinking of the said materials.

The compounds of formula (I) can be incorporated in the polymeric materials in the pure form or encapsulated in waxes, oils or polymers.

The compounds of formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilised with the products of formula (I) can be used for the production of mouldings, films, tapes, monofilaments, fibres, surface coatings and the like.

If desired, other conventional additives for synthetic polymers, such as antioxidants, UV absorbers, nickel stabilisers, pigments, fillers, plasticisers, antistatic agents, flameproofing agents, lubricants, corrosion inhibitors and metal deactivators, can be added to the mixtures of the compounds of formula (I) with the organic materials.

Particular examples of additives which can be used in admixture with the compounds of formula (I) are: 1. Antioxidants 1.1. Alkylated monophenols, for example 2,6-ditert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)- 4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example, 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl- 4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl- 4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-disec-amylphenol), 4,4'-bis-(2,6-dimethyl- 4-hydroxyphenyl) disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[ 6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl- 2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis( 3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-5-tert-butyl-4-hydroxy2-methylphenyl)-4-n-dodecylmercaptobutane, 1,1, 5,5-tetra-(5-tert-butyl- 4-hydroxy2-methylphenyl)pentane.

1.6. O-, N- and S-benzyl compounds, for example 3,5,3', 5'-tetra-tert-butyl-4,4'-dihydroxydibenzyl ether, octadecyl-4-hydroxy-3,5-dimethylbenzylmercaptoacetate, tris-(3,5-di-tert-butyl- 4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl- 4-hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3,5-tris-(3,5-di-tert-butyl-4-hydroxybenzyl)- 2,4,6-trimethylbenzene, 1,4-bis(3,5-di-tert-butyl-4-hydroxybenzyl)-2, 3,5,6-tetramethylbenzene, 2,4,6-tris(3,5-di-tert-butyl-4-hydroxybenzyl)phenol.

1.9. Triazine Compounds, for example 2,4-bis(octylmercapto)-6-(3,5-di-tert-butyl-4-hydroxyanilino)- 1,3,5-triazine, 2-octylmercapto-4,6-bis(3,5-di-tert-butyl-4-hydroxyanilino)- 1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4, 6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl- 4-hydroxybenzylphosphonate, dioctadecyl-5-tert-butyl-4-hydroxy3-methylbenzylphosphate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(3,5-dicyclohexyl-4-hydroxyphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.16. Amides of β-(3,5-di-tert-butyl-4-hydroxyphenyl)propionic acid e.g. N,N'-bis( 3,5-di-tert-butyl-4-hydroxyphenylpropionyl)trimethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)- 5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]- 2H-benzotriazole with polyethylene glycol 300; [R—CH$_2$CH$_2$—COO(CH$_2$)$_3$┤$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tertbutylbenzoyl) resorcinol, benzoyl resorcinol, 2,4-di-tertbutylphenyl 3,5-di-tert-butyl 4-hydroxybenzoate, hexadecyl 3,5-di-tert-butyl-4-hydroxybenzoate, octadecyl 3,5-di-tert-butyl- 4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy- 3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)- 2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy- 2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino- 2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl- 1,3,8-triazaspiro[4.5]decane-2,4-dione, 3-dodecyl-1-(2,2,6,6-tetramethyl-4-piperidyl)pyrrolidin-2, 5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho-and para-methoxy-disubstituted oxanilides and mixtures of o- and p-ethoxy disubstituted oxanilides.

2.8. 2-(2-Hydroxyphenyl)-1,3,5-triazines, for example 2,4,6-tris(2-hydroxy-4-octyloxyphenyl)- 1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(ten-butylphenyl)pentaerythritol diphosphite, tristearyl sorbitol triphosphite, tetrakis(2,4-di-tert-butylphenyl) 4,4'-biphenylene diphosphonite, 6-isooctyloxy- 2,4,8,10-tetratert-butyl-12H-dibenz[d,g]-1,3,2-dioxaphosphocin, 6-fluoro-2,4,8,10-tetra-tert-butyl- 12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

4a. Hydroxylamines, for example dibenzylhydroxylamine, dioctylhydroxylamine, didodecylhydroxylamine, ditetradecylhydroxylamine, dihexadecylhydroxylamine, dioctadecylhydroxylamine, 1-hydroxy-2,2,6,6-tetramethyl-4-piperidyl benzoate or bis (1-hydroxy-2,2,6,6-tetramethyl-4-piperidyl) sebacate.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. Nos. 4,325,863, 4,338,244 or 5,175,312, or 3-[4-(2-acetoxyethoxy)phenyl]-5,7-di-tert-butyl-benzofuran- 2-one 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran- 2-one.

The compounds of the formula (I) can also be used as stabilizers, especially as light stabilizers, for almost all materials known in the art of photographic reproduction and other reproduction techniques as e.g. described in Research Disclosure 1990, 31429 (pages 474 to 480).

In order to illustrate the present invention more clearly, there will now be described some examples of the preparation and of the use of the compounds of formula (I); these examples are given purely by way of illustration and do not imply any limitation.

EXAMPLE 1

16.30 g (0.04 mol) of 1-(2,2,6,6-tetramethyl-4-piperidyl)-3-[2-(2,2,6,6-tetramethyl-4-piperidylamino)ethyl]-2-imidazolidinone are added slowly to a solution of 7.38 g (0.04 mol) of cyanuric chloride in 70 ml of xylene whilst keeping the temperature between 0° and 5° C.

When the addition is complete, the mixture is stirred for 1 hour at about 10° C., 5.10 g (0.042 mol) of a 33% aqueous sodium hydroxide solution are added whilst keeping the temperature at 0° C., and the mixture is stirred for a further hour at between 0° and 20° C.

17.37 g (0.044 mol) of N,N'-bis(2,2,6,6-tetramethyl-4-piperidyl)-1,6-hexanediamine are added and the mixture is heated for 2 hours at 60° C.

Thereafter 4.8 g (0.12 mol) of crushed sodium hydroxide are added and the mixture is heated for one hour under reflux and for 12 hours under reflux with azeotropic removal of water.

After cooling to 60° C., the reaction mixture is stirred with 15 ml of water, heated under reflux with azeotropic removal of the added water, filtered and evaporated under reduced pressure. A product with melting point 116°–120° C. and molecular weight $\overline{M}n=1800$ is obtained, which contains recurring units of the formula

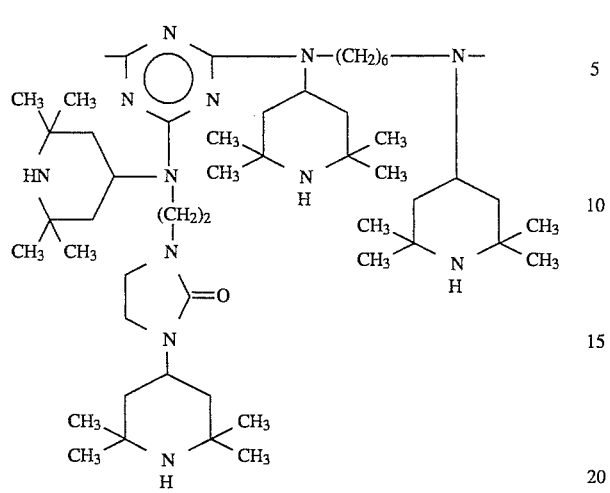

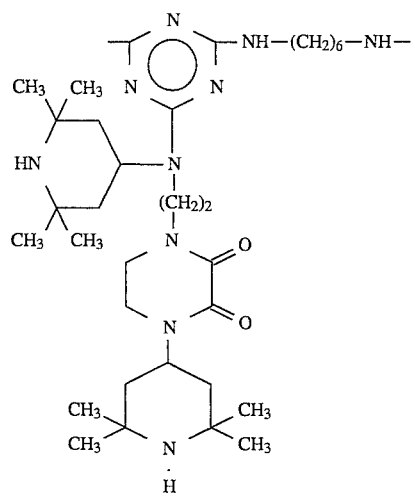

EXAMPLE 2

Following the procedure described in Example 1, reaction of 17.43 g (0.04 mol) of 1-(2,2,6,6-tetramethyl-4-piperidyl)-4-[2-(2,2,6,6-tetramethyl-4-piperidylamino)ethyl]-2,3-piperazinedione with 7.38 g (0.04 mol) of cyanuric chloride and 17.37 g (0.044 mol) of N,N'-bis(2,2,6,6-tetramethyl-4-piperidyl)-1,6-hexanediamine gives a product of melting point 120°–124° C. and molecular weight $\overline{Mn}=2600$, containing recurring units of formula

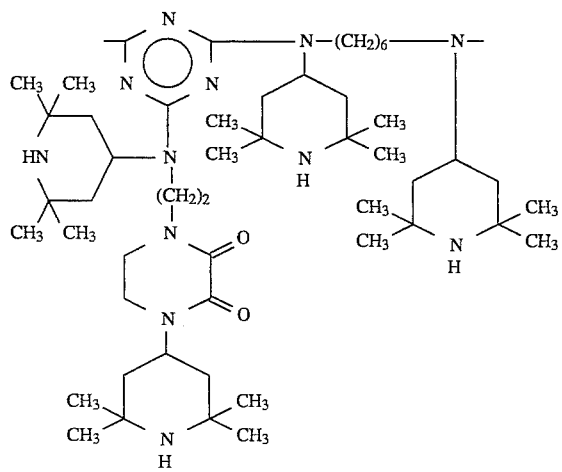

EXAMPLE 3

Following the procedure described in Example 1, reaction of 17.43 g (0.04 mol) of 1-(2,2,6,6-tetramethyl-4-piperidyl)-4-[2-(2,2,6,6-tetramethyl-4-piperidylamino)ethyl]-2,3-piperazinedione with 7.38 g (0.04 mol) of cyanuric chloride and 5.10 g (0,044 mol) of 1,6-hexanediamine gives a product of melting point 190°–195° C. and molecular weight $\overline{Mn}=2560$, containing recurring units of formula

EXAMPLE 4

Following the procedure described in Example 1, reaction of 16.30 g (0.04 mol) of 1-(2,2,6,6-tetramethyl-4-piperidyl)-3-[2-(2,2,6,6-tetramethyl-4-piperidylamino)ethyl]-2-imidazolidinone with 7.38 g (0.04 mol) of cyanuric chloride and 5.68 g (0.044 mol) of 1-piperazineethanamine, gives a product of melting point 192°–194° C. and molecular weight $\overline{Mn}=5900$, containing recurring units of formula

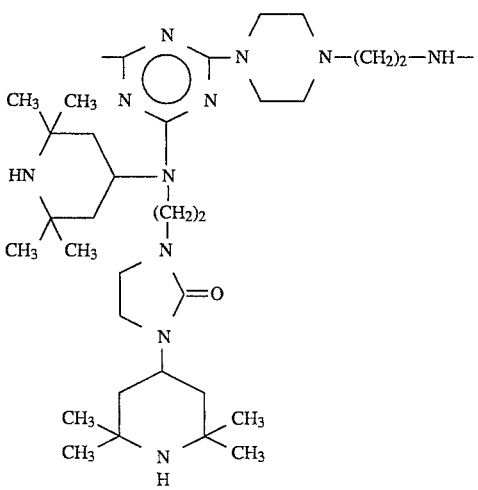

EXAMPLE 5

Following the procedure described in example 1, reaction of 16.30 g (0.04 mol) of 1(2,2,6,6-tetramethyl-4-piperidyl)-3[2(2,2,6,6-tetramethyl-4-piperidylamino)-ethyl]- 2-imidazolidone with 7.38 g (0.04 mol) of cyanuric chloride, 7.89 g (0.02 mol) of N,N'-bis(2,2,6,6-tetramethyl-4-piperidyl)-1,6-hexandiamine and 2.23 g (0.025 mol) of 2-ethylaminoethanol, gives a product of melting point 160°–164 ° C. and molecular weight $\overline{Mn}=1680$, containing recurring units of formulae

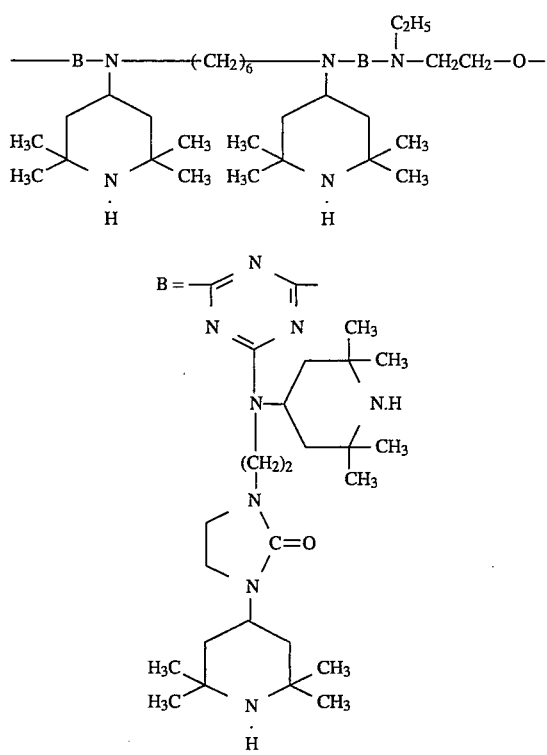

EXAMPLE 6

Following the procedure described in example 1, reaction of 16.30 g (0.04 mol) of 1(2,2,6,6-tetramethyl-4-piperidyl)-3[2(2,2,6,6-tetramethyl-4-piperidylamino)-ethyl]- 2-imidazolidone with 7.38 g (0.04 mol) of cyanuric chloride and 5.10 g (0.04 mol) of 1,6-hexandiamine gives a product of melting point 148°–151 °C. and molecular weight $\overline{Mn}=2360$, containing recurring units of formulae

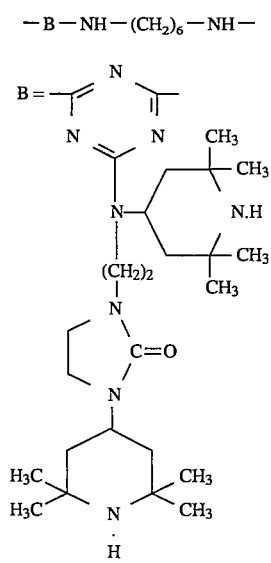

EXAMPLE 7

(Light stabilising action in polypropylene fibres) 2.5 g of one of the products indicated in Table 1, 1 g of tris(2,4-di-tert-butylphenyl) phosphite, 0.5 g of calcium monoethyl 3,5-di-tert-butyl-4-hydroxybenzylphosphonate, 1 g of calcium stearate and 2.5 g of titanium dioxide are mixed in a slow mixer with 1000 g of polypropylene powder having a melt index=12 g/10 min (measured at 230° C. and 2.16 kg).

The mixtures are extruded at 200°–230° C. to give polymer granules which are subsequently converted to fibres using a semi-industrial type of apparatus (Leonard-Sumirago (VA) Italy) and operating under the following conditions:

extruder temperature: 200°–230° C.

head temperature: 255°–260° C.

stretch ratio: 1:3.5 gauge: 11 dtex per filament

The fibres thus prepared are mounted on white cardboard and then exposed in a Weather-O-Meter model 65 WR (ASTM D2565-85) with a black panel temperature of 63° C.

The residual tenacity is measured, on samples taken after various light exposure times, by means of a constant speed tensometer, from which the exposure time, in hours, needed to halve the initial tenacity ($T_{50}$) is calculated. By way of comparison, the fibres prepared under the same conditions as those given above, but without the addition of stabilisers of the invention, were exposed.

The results obtained are reported in Table 1.

TABLE 1

| Stabiliser | $T_{50}$ (hours) |
|---|---|
| without stabiliser | 170 |
| compound of Example 1 | >1800 |
| compound of Example 2 | 1730 |
| compound of Example 3 | 990 |
| compound of Example 4 | 960 |

What is claimed is:

1. A compound of formula (I)

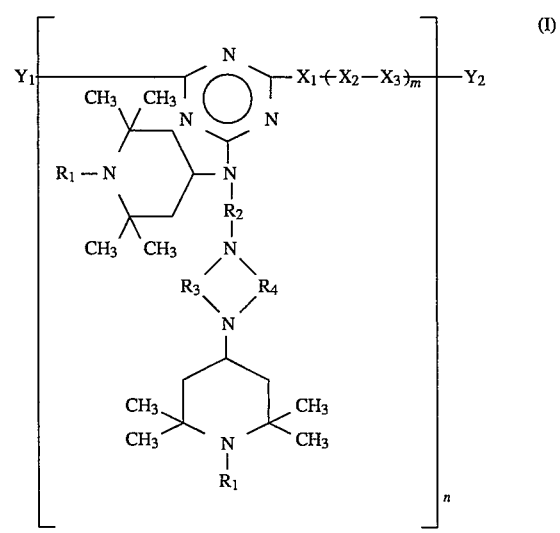

in which $R_1$ is hydrogen, $C_1$–$C_8$alkyl, O., OH, $CH_2CN$, $C_1$–$C_{18}$alkoxy, $C_5$–$C_{12}$cycloalkoxy, $C_3$–$C_6$alkenyl, or $C_7$–$C_9$phenylalkyl, which is unsubstituted or substituted on the phenyl by 1, 2 or 3 $C_1$–$C_4$alkyls, or $C_1$–$C_8$acyl;

$R_2$ and $R_3$, which may be identical or different, are $C_2$-$C_3$alkylene;

$R_4$ is —CO—, —COCO—, —COCH$_2$CO— or —CH$_2$CO—;

$X_1$ and $X_3$, which may be identical or different, are one of the groups of the formula (IIa)–(IIe)

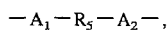  (IIa)

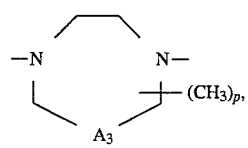  (IIb)

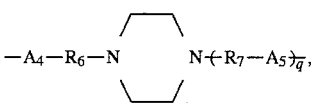  (IIc)

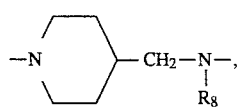  (IId)

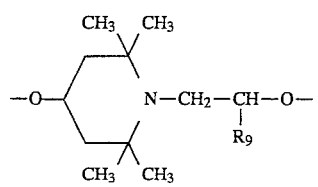  (IIe)

in which $A_1$, $A_2$, $A_4$ and $A_5$, which may be identical or different, are —O— or

where $R_{10}$ is hydrogen, $C_1$-$C_{18}$alkyl, $C_5$-$C_{12}$cycloalkyl which is unsubstituted or substituted by 1, 2 or 3 $C_1$-$C_4$alkyls, $C_7$-$C_9$phenylalkyl which is unsubstituted or substituted on the phenyl by 1, 2 or 3 $C_1$-$C_4$alkyls, or a group of the formula (III)

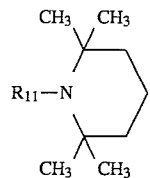  (III)

where $R_{11}$ has any one of the meanings given for $R_1$; $R_5$ is $C_2$-$C_{12}$alkylene, $C_4$-$C_{12}$alkylene interrupted by 1, 2 or 3 oxygen atoms or by 1 or 2

groups, where $R_{12}$ has any one of the meanings given for $R_{10}$ or is $C_1$-$C_8$acyl or ($C_1$-$C_8$alkoxy)carbonyl, or $R_5$ is $C_5$-$C_7$cycloalkylene, $C_5$-$C_7$cycloalkylenedi($C_1$-$C_4$alkylene), $C_1$-$C_4$alkylenedi($C_5$-$C_7$cycloalkylene), $C_2$-$C_4$alkylidenedi($C_5$-$C_7$cycloalkylene), phenylene, phenylenedi($C_1$-$C_4$alkylene), $C_1$-$C_4$alkylenediphenylene or $C_2$-$C_4$alkylidenediphenylene, each phenylene group being unsubstituted or substituted by 1 or 2 $C_1$-$C_4$alkyls, or $R_5$ is a group of the formula (IV)

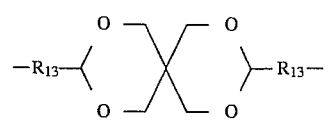  (IV)

where $R_{13}$ is $C_2$-$C_6$alkylene; $A_3$ is a direct bond or —CH$_2$—, p is zero, 1, 2 or 3; $R_6$ and $R_7$, which may be identical or different, are $C_2$-$C_6$alkylene, q is zero or 1; $R_8$ is as defined above for $R_{10}$ and $R_9$ is hydrogen or $C_1$-$C_4$alkyl; $X_2$ is $C_2$-$C_{12}$alkylene, $C_4$-$C_{12}$alkylene interrupted by 1, 2 or 3 oxygen atoms, 2-hydroxytrimethylene, phenylenedimethylene, carbonyl or one of the groups of the formula (Va)–(Ve)

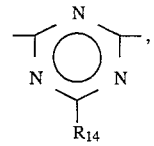  (Va)

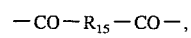  (Vb)

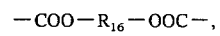  (Vc)

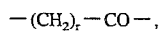  (Vd)

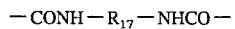  (Ve)

in which $R_{14}$ is one of the groups of the formula (VIa)–(VId)

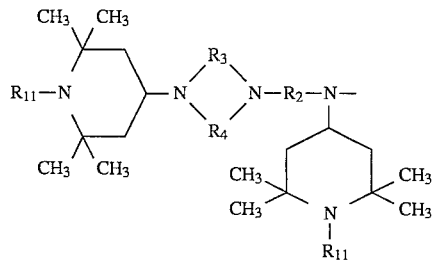  (VIa)

-continued

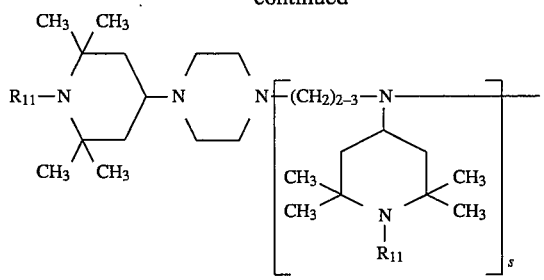
(VIb)

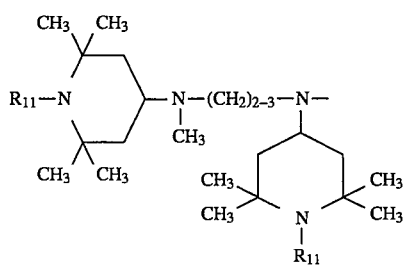
(VIc)

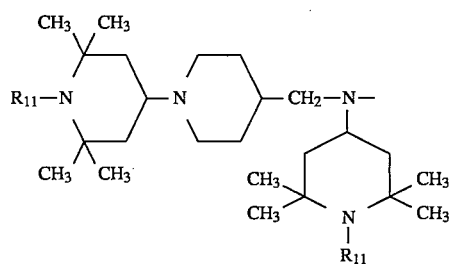
(VId)

where $R_2$, $R_3$, $R_4$ and $R_{11}$ are as defined above and s is zero or 1, or $R_{14}$ is a group of formula (VII)

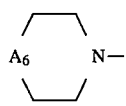
(VII)

where $A_6$ is a direct bond, —O—, —CH$_2$—, —CH$_2$CH$_2$— or

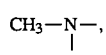

or $R_{14}$ is an $R_{18}$O— or

group, where $R_{18}$, $R_{19}$ and $R_{20}$, which may be identical or different, have any one of the meanings given for $R_{10}$ or are $C_3$–$C_{18}$alkenyl, tetrahydrofurfuryl, phenyl which is unsubstituted or substituted by 1, 2 or 3 $C_1$–$C_4$alkyls or by $C_1$–alkoxy, or $C_2$–$C_4$alkyl which is substituted in the 2, 3 or 4-position by $C_1$–$C_8$alkoxy or by di($C_1$–$C_4$alkyl)amino or by a group of formula (VII); $R_5$ is a direct bond, $C_1$–$C_{12}$alkylene, $C_2$–$C_{20}$alkylidene, cyclohexylene, methylcyclohexylene or phenylene; $R_{16}$ has any one of the meanings given for $R_5$, r is an integer from 1 to 10 and $R_{17}$ has any one of the meanings given for $R_5$ or is

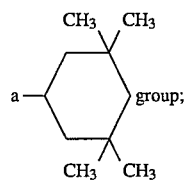
group;

m is zero, 1,2, 3 or 4 and n is a number from 1 to 50 with the restriction that n is 1 only if m is other than zero;

$Y_1$ is Cl, OH, ONa, OK, an $R_{14}$ group or a —$X_1$Z or —$X_3$Z group, where Z is hydrogen, methyl, benzyl, $C_1$–$C_8$acyl or ($C_1$–$C_8$alkoxy)carbonyl and $Y_2$ is Z, a

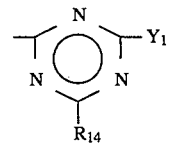

group or an —$X_2$OH group.

2. A compound of formula (I) according to claim 1, in which $R_1$ and $R_{11}$, which may be identical or different, are hydrogen, $C_1$–$C_4$alkyl, OH, $C_6$–$C_{12}$alkoxy, $C_5$–$C_8$cycloalkoxy, allyl, benzyl or acetyl.

3. A compound of formula (I) according to claim 1, in which $R_2$ and $R_3$, which may be identical or different, are $C_2$–$C_3$alkylene, $R_4$ is —CO—, —COCO— or —COCH$_2$CO—;

$X_1$ and $X_3$, which may be identical or different, are one of the groups of formula (IIa)–(IIe), in which $A_1$, $A_2$, $A_4$ and $A_5$, which may be identical or different, are —O— or

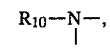

where $R_{10}$ is hydrogen, $C_1$–$C_{12}$alkyl, $C_5$–$C_8$cycloalkyl which is unsubstituted or substituted by 1, 2 or 3 $C_1$–$C_4$alkyls, benzyl which is unsubstituted or substituted on the phenyl by 1, 2 or 3 $C_1$–$C_4$alkyls, or a group of formula (III), $R_5$ is $C_2$–$C_{10}$alkylene, $C_4$–$C_{10}$alkylene interrupted by 1, 2 or 3 oxygen atoms or by 1 or 2

groups, where $R_{12}$ has any one of the meanings given for $R_{10}$ or is $C_1$–$C_4$acyl or ($C_1$–$C_4$alkoxy)carbonyl, or $R_5$ is cyclohexylene, cyclohexylenedimethylene, methylenedicyclohexylene, isopropylidenedicyclohexylene, phenylene, methylphenylene, phenylenedimethylene, methylenediphenylene or isopropylidenediphenylene, or $R_5$ is a group of formula (IV), where $R_{13}$ is $C_2$–$C_4$alkylene; $A_3$ is a direct bond or —CH$_2$—, p is zero, 1, 2 or 3, $R_6$ and $R_7$, which may be identical or different, are $C_2$–$C_4$alkylene, q is zero or 1, $R_8$ is as defined above for $R_{10}$ and $R_9$ is hydrogen or $C_1$–$C_4$alkyl;

$X_2$ is $C_2$–$C_{10}$alkylene, $C_4$–$C_{10}$alkylene interrupted by 1, 2 or 3 oxygen atoms, 2-hydroxytrimethylene, phenylenedimethylene or one of the groups of formula (Va)–(Ve), in which $R_{14}$ is one of the groups of formula (VIa)–(VId), where $R_2$, $R_3$ and $R_4$ are as defined above and s is zero or 1, or $R_{14}$ is 1-pyrrolidyl, 1-piperidyl, 4-morpholinyl or 1-hexahydroazepinyl or an $R_{18}$O— or

group, where $R_{18}$, $R_{19}$ and $R_{20}$, which may be identical or different, have any one of the meanings given for $R_{10}$ or are $C_3$–$C_{12}$alkenyl, tetrahydrofurfuryl, phenyl which is unsubstituted or substituted by 1, 2 or 3 $C_1$–$C_4$alkyls, or $C_2$–$C_3$alkyl substituted in the 2 or 3 position by $C_1$–$C_4$alkoxy or by di($C_1$–$C_4$alkylamino) or by a 1-pyrrolidyl, 1-piperidyl, 4-morpholinyl or 1-hexahydroazepinyl group; $R_{15}$ is a direct bond, $C_1$–$C_{10}$alkylene, $C_2$–$C_{14}$alkylidene, cyclohexylene or phenylene; $R_{16}$ has any one of the meanings given for $R_5$, r is an integer from 1 to 5 and $R_{17}$ has any one of the meanings given for $R_5$ or is a

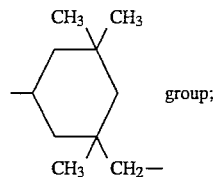

group;

m is zero, 1, 2 or 3 and n is a number from 1 to 30, with the restriction that n is 1 only if m is other than zero;

$Y_1$ is Cl, OH, ONa, OK, an $R_{14}$ group or a —$X_1Z$ or —$X_3Z$ group, where Z is hydrogen, methyl, benzyl, $C_1$–$C_4$acyl or ($C_1$–$C_4$alkoxy)carbonyl and $Y_2$ is Z, a

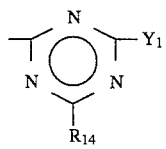

group or an —$X_2$OH group.

4. A compound of formula (I) according to claim 1, in which $R_2$ and $R_3$, which may be identical or different, are $C_2$–$C_3$alkylene and $R_4$ is —CO— or —COCO—;

$X_1$ and $X_3$, which may be identical or different, are one of the groups of formula (IIa)–(IIe) in which $A_1$, $A_2$, $A_4$ and $A_5$, which may be identical or different, are —O— or

where $R_{10}$ is hydrogen, $C_1$–$C_8$alkyl, cyclohexyl which is unsubstituted or substituted by 1, 2 or 3 $C_1$–$C_4$alkyls, benzyl or a group of formula (III); $R_5$ is $C_2$–$C_8$alkylene, $C_4$–$C_{10}$alkylene interrupted by 1, 2 or 3 oxygen atoms or by an

group, where $R_{12}$ is hydrogen, methyl, acetyl or ($C_1$–$C_2$alkoxy)carbonyl, or $R_5$ is cyclohexylene, cyclohexylenedimethylene, methylenedicyclohexylene, phenylenedimethylene or isopropylidenediphenylene, or $R_5$ is a group of formula (IV), where $R_{13}$ is $C_3$–$C_4$alkylene;

$A_3$ is a direct bond or —$CH_2$—, p is zero or 1, $R_6$ and $R_7$, which may be identical or different, are $C_2$–$C_3$alkylene, q is zero or 1, $R_8$ is as defined above for $R_{10}$ and $R_9$ is hydrogen or methyl;

$X_2$ is $C_2$–$C_8$alkylene, $C_4$–$C_8$alkylene interrupted by 1 or 2 oxygen atoms, 2-hydroxytrimethylene, phenylenedimethylene or one of the groups of formula (Va)–(Ve) in which $R_{14}$ is one of the groups of formula (VIa)–(VId), where $R_2$, $R_3$ and $R_4$ are as defined above and s is zero or 1, or $R_{14}$ is a 4-morpholinyl group or an $R_{18}$O— or

group, where $R_{18}$, $R_{19}$ and $R_{20}$, which may be identical or different, have any one of the meanings given for $R_{10}$ or are allyl, undecenyl, tetrahydrofurfuryl, phenyl or $C_2$–$C_3$alkyl, substituted in the 2 or 3 position by $C_1$–$C_4$alkoxy, by dimethylamino, by diethylamino or by a 4-morpholinyl group; $R_{15}$ is a direct bond, $C_1$–$C_8$alkylene, $C_2$–$C_6$alkylidene, cyclohexylene or phenylene; $R_{16}$ is $C_2$–$C_8$alkylene, $C_4$—$C_{10}$alkylene interrupted by 1, 2 or 3 oxygen atoms, cyclohexylenedimethylene, isopropylidenedicyclohexylene or isopropylidenediphenylene, r is an integer from 1 to 4, $R_{17}$ has any one of the meanings given for $R_5$ or is methylphenylene, methylenediphenylene or a

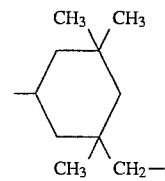

group;

m is zero, 1 or 2 and n is a number from 1 to 20 with the restriction that n is 1 only if m is other than zero;

$Y_1$ is OH, ONa, OK, an $R_{14}$ group or an —$X_1Z$ or —$X_3Z$ group, where Z is hydrogen, methyl, acetyl or ($C_1$–$C_4$alkoxy)carbonyl and $Y_2$ is Z, a

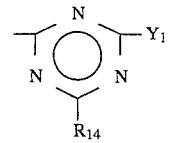

group or a —$X_2$OH group.

5. A compound of formula (I) according to claim 1, in which $R_2$ and $R_3$, which may be identical or different, are ethylene or trimethylene and $R_4$ is —CO— or —COCO—;

$X_1$ and $X_3$, which may be identical or different, are one of the groups of formula (IIa)–(IIe) in which $A_1$, $A_2$, $A_4$ and $A_5$, which may be identical or different, are —O— or

where $R_{10}$ is hydrogen, $C_1$–$C_4$alkyl, cyclohexyl, benzyl or a group of formula (III); $R_5$ is $C_2$–$C_6$alkylene, $C_6$–$C_{10}$alkylene interrupted by 2 or 3 oxygen atoms, cyclohexylenedimethylene, methylenedicyclohexylene or phenylenedimethylene, or $R_5$ is a group of formula (IV), where $R_{13}$ is trimethylene; $A_3$ is a direct bond, p is zero or 1, $R_6$ and $R_7$, which may be identical or different, are ethylene or trimethylene, q is zero or 1, $R_8$ is as defined above for $R_{10}$ and $R_9$ is hydrogen or methyl;

$X_2$ is $C_2$–$C_6$alkylene, 2-hydroxytrimethylene, phenylenedimethylene or one of the groups of formula (Va)–(Ve) in which $R_{14}$ is a group of formula (VIa), with $R_2$, $R_3$ and $R_4$ as defined above, or a 4-morpholinyl group or an $R_{18}$O— or

group, where $R_{18}$ is $C_1$–$C_4$alkyl, cyclohexyl, allyl, phenyl, benzyl or a group of formula (III) and $R_{19}$ and $R_{20}$, which may be identical or different, are as defined above for $R_{10}$; $R_{15}$ is a direct bond or $C_1$–$C_6$alkylene, $R_{16}$ is $C_4$–$C_6$alkylene, r is 1 or 2 and $R_{17}$ is $C_2$–$C_6$alkylene or a

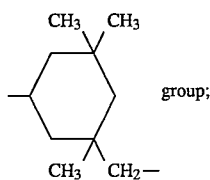

group;

m is zero, 1 or 2 and n is a number from 1 to 15 with the restriction that n is 1 only if m is other than zero;

$Y_1$ is OH, ONa, OK, an $R_{14}$ group or an —$X_1Z$ or —$X_3Z$ group, where Z is hydrogen, methyl, acetyl or ($C_1$–$C_2$alkoxy)carbonyl and $Y_2$ is Z, a

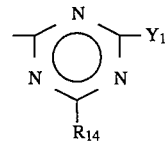

group or an —$X_2$OH group.

6. A compound of formula (I) according to claim 1, in which $R_1$ and $R_{11}$, which may be identical or different, are hydrogen or methyl, $R_2$ and $R_3$ are ethylene, $R_4$ is —CO— or —COCO—;

$X_1$ is one of the groups of formula (IIa)–(IIc) in which $A_1$, $A_2$ and $A_4$ are an

group, where $R_{10}$ is hydrogen, methyl, ethyl or a group of formula (III), or $A_2$ is —O—; $R_5$ is —$(CH_2)_{2-6}$— or —$(CH_2)_3$—O—$(CH_2)_{2-4}$—O—$(CH_2)_3$—; $A_3$ is a direct bond, p and q are zero and $R_6$ is ethylene;

n is a number from 2 to 10, $Y_1$ is OH, ONa, OK, an $R_{14}$ group or a —$X_1Z$ group, with Z being hydrogen or methyl, and $Y_2$ is hydrogen, methyl or a

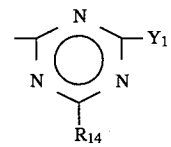

group and $R_{14}$ is a group of formula (VIa) with $R_2$, $R_3$, $R_4$ and $R_{11}$ as defined above.

* * * * *